US011964991B2

(12) United States Patent
Hong et al.

(10) Patent No.: US 11,964,991 B2
(45) Date of Patent: Apr. 23, 2024

(54) RUTHENIUM COMPLEX COMPOUND, LIGAND FOR PRODUCING SAME, AND USE THEREOF

(71) Applicant: GWANGJU INSTITUTE OF SCIENCE AND TECHNOLOGY, Gwangju (KR)

(72) Inventors: Sukwon Hong, Gwangju (KR); Seunghwan Byun, Gwangju (KR)

(73) Assignee: GWANGJU INSTITUTE OF SCIENCE AND TECHNOLOGY, Gwangju (KR)

(*) Notice: Subject to any disclaimer, the term of this patent is extended or adjusted under 35 U.S.C. 154(b) by 460 days.

(21) Appl. No.: 17/423,575

(22) PCT Filed: Jan. 17, 2020

(86) PCT No.: PCT/KR2020/000855
§ 371 (c)(1),
(2) Date: Jul. 16, 2021

(87) PCT Pub. No.: WO2020/149693
PCT Pub. Date: Jul. 23, 2020

(65) Prior Publication Data
US 2022/0111374 A1    Apr. 14, 2022

(30) Foreign Application Priority Data

Jan. 18, 2019    (KR) .................. 10-2019-0006790

(51) Int. Cl.
C07F 15/00    (2006.01)
B01J 31/22    (2006.01)
C07C 67/475    (2006.01)

(52) U.S. Cl.
CPC ....... C07F 15/0046 (2013.01); B01J 31/2226 (2013.01); B01J 31/2278 (2013.01);
(Continued)

(58) Field of Classification Search
CPC ............... C07F 15/0046; B01J 31/2226; B01J 31/2278; B01J 2231/54; B01J 2531/821; C07C 67/475
See application file for complete search history.

(56) References Cited

U.S. PATENT DOCUMENTS 9,328,132 B2 *  5/2016  Skowerski .......... C07F 15/0046

FOREIGN PATENT DOCUMENTS

CN          107987107 A       5/2018
KR     10-2015-0023672 A      3/2015
WO       2013-136978 A1       9/2013

OTHER PUBLICATIONS

Alcarazo, M., et al., Imidazo[1,5-a]pyridine: A Versatile Architecture for Stable N-Heterocyclic Carbenes, J. Am. Chem. Soc., vol. 127, No. 10, pp. 3290-3291 (Year: 2005).*

(Continued)

*Primary Examiner* — Yate' K Cutliff
(74) *Attorney, Agent, or Firm* — Hauptman Ham, LLP

(57) ABSTRACT

In a ruthenium complex compound according to the present invention, an NHC ligand has an excellent electron-donating ability to stabilize methylidene species due to the steric interaction between substituents having relatively different sizes. The ruthenium complex compound can improve selectivity when used as a catalyst due to having an asymmetric structure, and the activity of the ruthenium complex compound can be improved by adjusting substituents and additives. Accordingly, the ruthenium complex compound can be used as a catalyst in cross metathesis reactions including ethenolysis to produce desired compounds such as linear α-olefins at high yield, even under relatively mild conditions.

18 Claims, 2 Drawing Sheets

(52) U.S. Cl.
CPC ......... *C07C 67/475* (2013.01); *B01J 2231/54* (2013.01); *B01J 2531/821* (2013.01)

(56) References Cited

OTHER PUBLICATIONS

Kannenberg, A., et al., A novel Ligand for the Enantioselective Ruthenium-catalyzed Olefin Metathesis, Asymmetric Catalysis, Angew. Chem. INt. Ed., vol. 50, pp. 3299-3302 (Year: 2011).*
Kannenberg et al., "A Novel Ligand for the Enantioselective Ruthenium-Catalyzed Olefin Metathesis", Asymmetric Catalysis, Angew. Chem. Int. Ed. 2011, vol. 50, pp. 3299-3302, cited in NPL 5 & 6.
A. Pazio et al., "Nitrenium ions and trivalent boron ligands as analogues of N-heterocyclic carbenes in olefin metathesis; a computational study", Dalton Trans., 2015, vol. 44, pp. 20021-20026, cited in NPL 5 & 6.
Renee M. Thomas et al., "Highly Selective Ruthenium Metathesis Catalysts for Ethenolysis", Journal of the American Chemical Society. 2011, 133, pp. 7490-7496, cited in the specification.
Richard L. Pederson et al., "Ruthenium Olefin Metathesis Catalysts for the Ethenolysis of Renewable Feedstocks", Clean 2008, 36 (8), pp. 669-673, cited in the specification.
Korean Written Opinion dated Apr. 29, 2020, corresponding to International Application No. PCT/KR2020/000855.
International Search Report dated Apr. 29, 2020, corresponding to International Application No. PCT/KR2020/000855.

* cited by examiner

RUTHENIUM COMPLEX COMPOUND, LIGAND FOR PRODUCING SAME, AND USE THEREOF

CROSS-REFERENCE TO RELATED APPLICATION

The present application is a national stage filing under 35 U.S.0 § 371 of PCT application number PCT/KR2020/000855 filed on Jan. 17, 2020, which is based upon and claims the benefit of priorities to Korean Patent Application No. 10-2019-0006790 filed on Jan. 18, 2019, in the Korean Intellectual Property Office. Both of the aforementioned applications are hereby incorporated by reference in their entireties.

TECHNICAL FIELD

The present invention relates to a ruthenium complex compound, to a ligand for preparing the same, and to a use thereof. Specifically, the present invention relates to a novel ruthenium complex compound used as a catalyst with high selectivity and stability, to a ligand for preparing the same, and to a process for preparing a linear α-olefin using the same.

BACKGROUND ART

Linear α-olefins ($LAO_S$) having an olefin at the terminal are used as essential raw materials for various chemical products.

As a method of preparing a linear α-olefin from a petrochemical raw material, the Ziegler process of Scheme 1 and the Shell higher olefin process (SHOP) process of Scheme 2 shown below are known.

[Scheme 1]

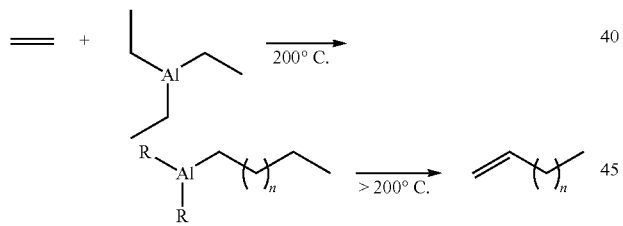

[Scheme 2]

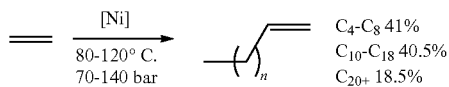

However, these conventional processes have a problem in that they require conditions of high temperature and high pressure and that the synthesized linear α-olefins have a wide carbon number distribution due to the oligomerization of ethylene.

Meanwhile, natural seed oil, instead of petroleum raw materials, may be used for the preparation of linear α-olefins. For example, it is possible to prepare a linear α-olefin having an olefin at the terminal such as 1-decene shown in Scheme 3 below by subjecting methyl oleate obtained from renewable seed oil raw materials and ethylene to cross-metathesis, that is, an ethenolysis reaction in the presence of a catalyst to cleave the internal carbon-carbon double bond and to form a new carbon-carbon double bond.

[Scheme 3]

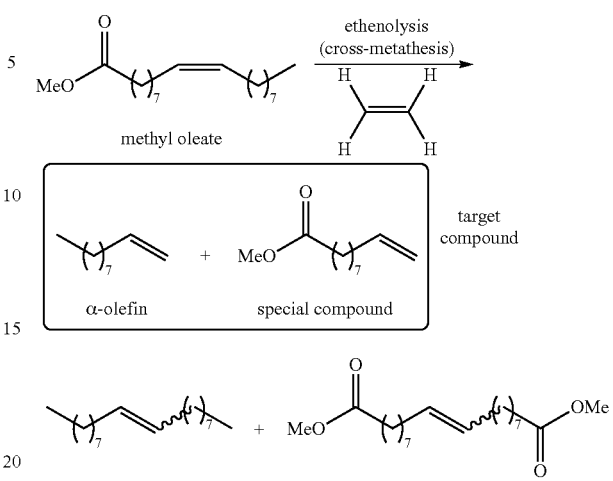

Such an ethenolysis reaction can be carried out under the mild conditions of a temperature of 25 to 100° C. and a pressure of 1 to 10 bar. It has an advantage in that the carbon number distribution of the synthesized linear α-olefin is narrow.

A ruthenium complex compound comprising a symmetrical N-heterocyclic carbene (NHC) ligand and a methylidene species is known as a catalyst used for the ethenolysis using ethylene (see Richard L. Pederson, et al., Clean 2008, 36 (8), 669-673).

In addition, a ruthenium complex having an asymmetrically substituted N-heterocyclic carbene ligand is known as a promising catalyst for ethenolysis with high selectivity for products of the cross-metathesis by ethylene as compared with by-products of the self-metathesis (see R. M. Thomas, et al., J. Am. Chem. Soc. 2011, 133, 7490-7496).

However, these conventional ruthenium complex compounds have problems in that they lack the electron donating ability to stabilize unstable methylidene species, resulting in low stability, and that the selectivity for a desired linear α-olefin is low. There is also room for improvement in the activity.

DISCLOSURE OF INVENTION

Technical Problem

Imidazo[1,5-a]pyridin-3-ylidene (ImPy), first reported in 2005, is a structurally asymmetric NHC ligand with various electronic properties. In particular, an ImPy ligand can be synthesized as an abnormal carbene (abnormal ImPy, aImPy) ligand having improved electron donating properties.

As a result of research on the effect of the structure of a ruthenium catalyst based on an aImPy ligand and its electronic properties on the catalytic activity, selectivity, and stability, the present inventors have been able to synthesize a novel ruthenium catalyst stable at high temperatures with high activity and selectivity. In addition, the present inventors have discovered that the activity can be further enhanced through additives.

Accordingly, an object of the present invention is to provide a novel ruthenium complex compound that can be advantageously used as a catalyst having high activity, selectivity, and stability.

Another object of the present invention is to provide a ligand for the preparation of the ruthenium complex compound.

Still another object of the present invention is to provide a catalyst having high activity and stability with high selectivity for the formation of an α-olefin, which comprises the ruthenium complex compound.

Still another object of the present invention is to provide a process for preparing a linear α-olefin with high efficiency using the catalyst.

Solution to Problem

In accordance with the above object, the present invention provides a ruthenium complex compound represented by the following Formula 1:

[Formula 1]

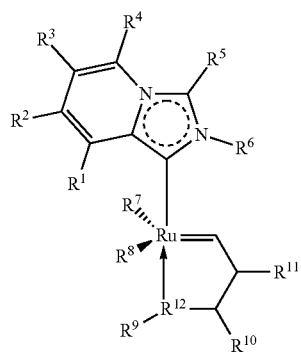

In the above formula, $R^1$ is halogen, amino, $C_{1-3}$ alkyl, or $C_{1-3}$ alkoxy;

$R^2$, $R^3$, and $R^4$ are each independently hydrogen, halogen, amino, $C_{1-5}$ alkyl, or $C_{1-5}$ alkoxy;

$R^5$ and $R^6$ are each independently a $C_{5-10}$ carbocycle or a 5-10-membered heterocycle;

$R^7$ and $R^8$ are each independently halogen;

$R^9$ is $C_{1-10}$ alkyl, a $C_{5-10}$ carbocycle, or a 5-10-membered heterocycle;

$R^{10}$ and $R^{11}$ are each independently $C_{1-10}$ alkyl or fused to each other to form a $C_{5-10}$ carbocycle or a 5-10-membered heterocycle; and $R^{12}$ is N or O;

wherein the alkyl and the alkoxy are each independently unsubstituted or substituted with at least one of halogen, hydroxy, and amino;

the carbocycle and the heterocycle are each independently a saturated or unsaturated ring, which is unsubstituted or substituted with at least one selected from the group consisting of halogen, nitro, $C_{1-5}$ alkyl, halo $C_{1-5}$ alkyl, $C_{1-5}$ alkoxy, and phenyl; and the heterocycle contains at least one heteroatom selected from N, S, and O.

In accordance with another object, the present invention provides a ligand for the preparation of a ruthenium complex compound, which comprises a compound represented by the following Formula 2:

[Formula 2]

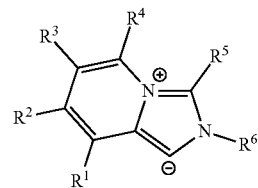

In the above formula, $R^1$ to $R^6$ are as defined in Formula 1 above.

In accordance with still another object, the present invention provides a catalyst comprising the ruthenium complex compound.

In accordance with still another object, the present invention provides a process for preparing a linear α-olefin, which comprises adding ethylene to an unsaturated fatty acid in the presence of the catalyst.

Advantageous Effects of Invention

The ruthenium complex compound of the present invention can exhibit high activity, selectivity, and stability when used as a catalyst. Specifically, the ruthenium complex compound can provide enhanced selectivity when acting as a catalyst by virtue of its asymmetric structure having substituents of relatively different sizes. In addition, the activity can be enhanced by virtue of the enhanced electron donating properties thanks to the abnormal structure of the ruthenium complex compound. The activity can be further enhanced through the control of additives. Accordingly, the ruthenium complex compound can be used as a catalyst for a cross-metathesis reaction including ethenolysis to produce a desired compound such as a linear α-olefin in high yield even under relatively mild conditions.

BEST MODE FOR CARRYING OUT THE INVENTION

Figure 1:
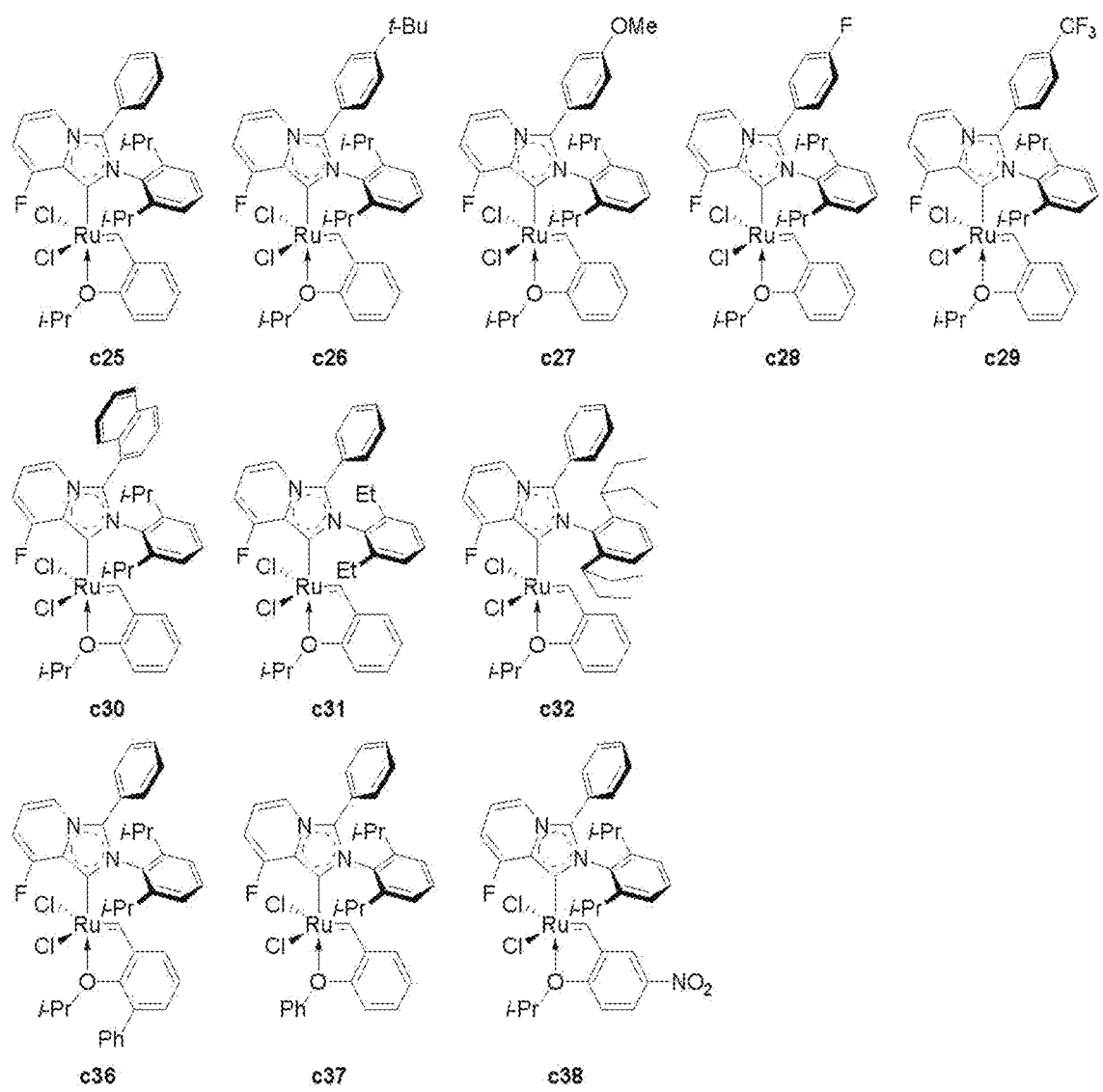
FIG. 1 shows the preparation and structure of the compounds of Formula 1 according to the Examples.

Hereinafter, the present invention will be described in detail.

As used herein, the term "halogen" may be fluorine, chlorine, bromine, or iodine, and it may be referred to as fluoro, chloro, bromo, or iodo as a substituent.

The term "alkyl" may refer to a straight-chain or branched hydrocarbon moiety. The alkyl may be composed of, for example, 1 to 10 carbons. In such a case, it may be expressed as "$C_{1-10}$ alkyl."

The terms "haloalkyl," "haloalkoxy," and the like may refer to alkyl, alkoxy, and the like, substituted with one or more halogens.

The term "carbocycle" refers to a saturated or unsaturated hydrocarbon ring, which may be aromatic or non-aromatic and may be monocyclic or polycyclic. The carbocycle may be, for example, a single/polycyclic ring composed of 5 to 10 carbons. In such a case, it may be expressed as a "$C_{5-10}$ carbocycle."

The term "heterocycle" refers to a saturated or unsaturated ring having one or more heteroatoms, which may be aromatic or non-aromatic and may be monocyclic or polycyclic. The heterocycle may be, for example, a single/polycyclic ring composed of 5 to 10 heteroatoms and/or carbon atoms. In such a case, it may be expressed as a "5-10-membered heterocycle."

The term "heteroatom" may be an atom selected from N, O, and S.

Ruthenium Complex Compound

The present invention provides a novel ruthenium complex compound.

The ruthenium complex compound according to an embodiment of the present invention is represented by the following Formula 1:

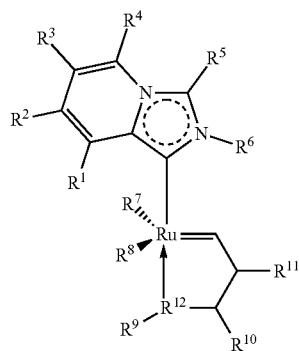

[Formula 1]

In the above formula, $R^1$ is halogen, amino, $C_{1-3}$ alkyl, or $C_{1-3}$ alkoxy;

$R^2$, $R^3$, and $R^4$ are each independently hydrogen, halogen, amino, $C_{1-5}$ alkyl, or $C_{1-5}$ alkoxy;

$R^5$ and $R^6$ are each independently a $C_{5-10}$ carbocycle or a 5-10-membered heterocycle;

$R^7$ and $R^8$ are each independently halogen;

$R^9$ is $C_{1-10}$ alkyl, a $C_{5-10}$ carbocycle, or a 5-10-membered heterocycle;

$R^{10}$ and $R^{11}$ are each independently $C_{1-10}$ alkyl or fused to each other to form a $C_{5-10}$ carbocycle, or a 5-10-membered heterocycle; and $R^{12}$ is N or O;

wherein the alkyl and the alkoxy are each independently unsubstituted or substituted with at least one of halogen, hydroxy, and amino;

the carbocycle and the heterocycle are each independently a saturated or unsaturated ring, which is unsubstituted or substituted with at least one selected from the group consisting of halogen, nitro, $C_{1-5}$ alkyl, halo $C_{1-5}$ alkyl, $C_{1-5}$ alkoxy, and phenyl; and the heterocycle contains at least one heteroatom selected from N, S, and O.

In an example of Formula 1, $R^1$ is halogen, more specifically fluoro.

In another example of Formula 1, $R^2$ and $R^4$ are hydrogen.

In still another example of Formula 1, $R^3$ is hydrogen or $C_{1-5}$ alkyl.

In still another example of Formula 1, $R^5$ and $R^6$ are each independently a $C_{6-10}$ carbocycle or a 5-10-membered heterocycle having aromaticity, wherein the carbocycle and the heterocycle are each independently unsubstituted or substituted with at least one selected from the group consisting of halogen, nitro, $C_{1-5}$ alkyl, halo $C_{1-5}$ alkyl, and $C_{1-5}$ alkoxy.

In still another example of Formula 1, $R^5$ and $R^6$ are each independently an aromatic $C_{6-10}$ carbocycle, wherein the carbocycles are each independently unsubstituted or substituted with one or more $C_{1-5}$ alkyl.

In still another example of Formula 1, $R^7$ and $R^8$ are chloro.

In still another example of Formula 1, $R^9$ is $C_{1-10}$ alkyl or a $C_{5-10}$ carbocycle, more specifically branched $C_{3-5}$ alkyl or an aromatic $C_{6-10}$ carbocycle.

In still another example of Formula 1, $R^{10}$ and $R^{11}$ are fused to each other to form an aromatic $C_{6-10}$ carbocycle, which is unsubstituted or substituted with phenyl.

The ruthenium complex compound of Formula 1 may comprise a mesoionic structure.

In addition, the ruthenium complex compound of Formula 1 may comprise a carbene ligand having an abnormal structure.

Specifically, the ruthenium complex compound of Formula 1 comprises an abnormal imidazo[1,5-a]pyridin-3-ylidene (aImPy) structure having enhanced electron donating properties.

In Formula 1, since aImPy has excellent electron donating ability to stabilize methylidene species, the stability of the compound of Formula 1 may be enhanced.

In addition, the substituents such as $R^1$, $R^5$, $R^6$, and the like in Formula 1 above may be modified to adjust the steric effect.

In addition, since the aImPy ligand has an asymmetric structure, the selectivity may be enhanced when the compound of Formula 1 acts as a catalyst.

The ruthenium complex compound according to another embodiment of the present invention is represented by the following Formula 1a:

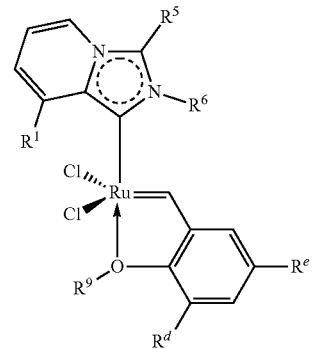

[Formula 1a]

In the above formula, $R^1$ is halogen, amino, $C_{1-3}$ alkyl, halo $C_{1-3}$ alkyl, or $C_{1-3}$ alkoxy;

$R^5$ and $R^6$ are each independently a $C_{5-10}$ carbocycle or a 5-10-membered heterocycle having aromaticity;

$R^9$ is $C_{1-3}$ alkyl or phenyl; and $R^d$ and $R^e$ are each independently hydrogen, nitro, or phenyl;

wherein the carbocycle and the heterocycle are each independently unsubstituted or substituted with at least one selected from the group consisting of halogen, nitro, $C_{1-5}$ alkyl, halo $C_{1-5}$ alkyl, and $C_{1-5}$ alkoxy; and the heterocycle contains at least one heteroatom selected from N, S, and O.

In an example of Formula 1a, W is halogen, more specifically fluoro.

In another example of Formula 1a, $R^5$ and $R^6$ are each independently a $C_{6-10}$ carbocycle or a 5-10-membered heterocycle having aromaticity, wherein the carbocycle and the heterocycle are each independently unsubstituted or substituted with at least one selected from the group consisting of halogen, nitro, $C_{1-5}$ alkyl, halo $C_{1-5}$ alkyl, and $C_{1-5}$ alkoxy.

In still another example of Formula 1a, $R^5$ and $R^6$ are each independently an aromatic $C_{6-10}$ carbocycle (e.g., a benzene or naphthalene ring), wherein the carbocycles are each independently unsubstituted or substituted with one or more $C_{1-5}$ alkyl.

The ruthenium complex compound according to still another embodiment of the present invention is represented by the following Formula 1b:

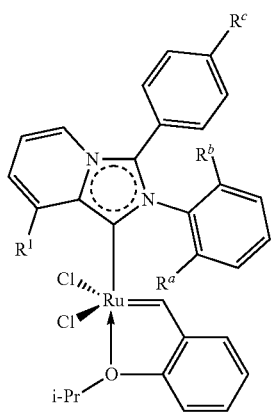

[Formula 1b]

In the above formula, $R^1$ is halogen; and $R^a$, $R^b$, and $R^c$ are each independently hydrogen, halogen, $C_{1-5}$ alkyl, halo $C_{1-5}$ alkyl, or $C_{1-5}$ alkoxy.

In an example of Formula 1b, $R^a$ and $R^b$ are each independently $C_{1-5}$ alkyl.

In another example of Formula 1b, $R^a$ and $R^b$ are each independently branched $C_{3-5}$ alkyl.

In still another example of Formula 1b, $R^c$ is hydrogen.

X-Ray Crystal Structure

Figure 2:
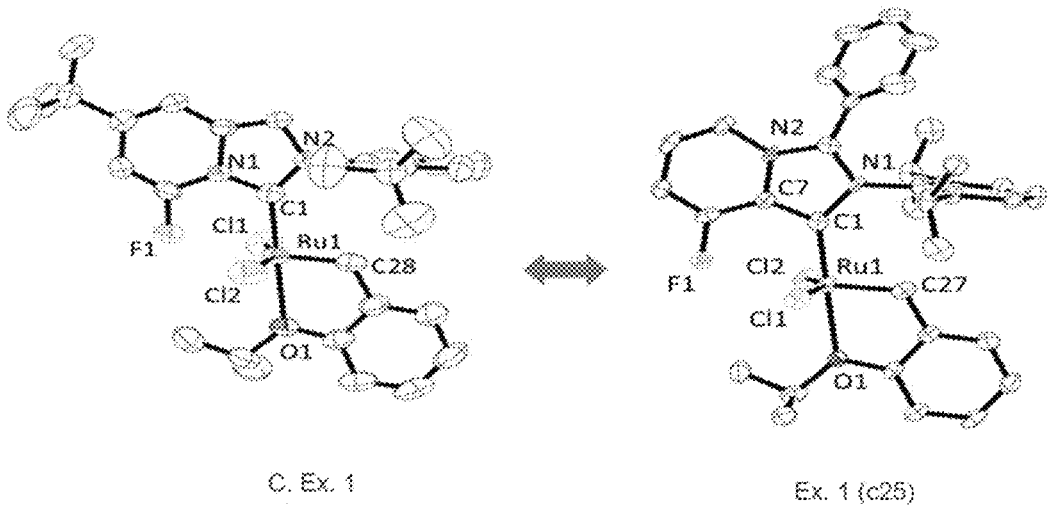
FIG. 2 shows the results of X-ray crystal analysis of the compounds of Comparative Example 1 and Example 1.

FIG. 2 shows the results of X-ray crystal structure analysis of the compound of Example 1.

The ruthenium complex compound may exhibit a distance of 2.85 to 3.15 Å or 2.7 to 3.0 Å between ruthenium (Ru) and substituent $R^1$ in X-ray crystal structure analysis.

In addition, the ruthenium complex compound may exhibit a distance of 2.28 to 2.32 Å between ruthenium (Ru) and oxygen (O) in X-ray crystal structure analysis.

Ligand The present invention also provides a ligand for the preparation of the ruthenium complex compound.

The ligand comprises a compound represented by the following Formula 2:

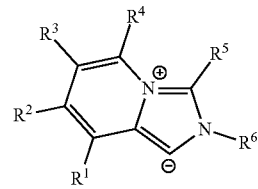

[Formula 2]

In the above formula, $R^1$ to $R^6$ are as defined in Formula 1 above.

In addition, more specific examples of $R^1$ to $R^6$ are as described above for the ruthenium complex compound.

The ligand of Formula 2 can be synthesized as a carbene ligand (aImPy) having a mesoionic or abnormal structure. It has enhanced electron donating properties. As a result, since the ligand has excellent electron donating ability to stabilize methylidene species, the stability of the ruthenium complex compound may be enhanced.

In addition, the substituents such as $R^1$, $R^5$, $R^6$, and the like in Formula 2 above may be modified to adjust the steric effect. In addition, since the ligand of Formula 2 has an asymmetric structure, the selectivity may be enhanced when the ruthenium complex compound acts as a catalyst.

Catalyst

The present invention also provides a catalyst comprising the ruthenium complex compound.

The catalyst may be used in a cross-metathesis reaction. For example, the catalyst may be used in a cross-metathesis reaction using an alkene compound.

As a specific example, the catalyst may be used in an alkenolysis reaction. Specifically, the catalyst may be used in an ethenolysis reaction using ethylene. More specifically, the catalyst may be used in an ethenolysis reaction of an unsaturated fatty acid such as methyl oleate.

As another specific example, the catalyst may be used in a metathesis reaction by ethenolysis of a linear or cyclic alkene compound.

As still another specific example, the catalyst may be used in an intramolecular cross-metathesis reaction, a ring-opening metathesis reaction, a ring-closing metathesis reaction, a ring-opening metathesis polymerization reaction, or acrylic diene-metathesis polymerization reaction.

As still another specific example, the catalyst may be used in a depolymerization reaction or an ethenolysis reaction of an unsaturated linear polymer containing a double bond.

In addition, the catalyst may further comprise one or more additional compounds for enhancing the catalytic activity in addition to the ruthenium complex compound. That is, the ruthenium complex compound may be used in combination with one or more additional compounds for enhancing the activity when used as a catalyst. The additional compound is not particularly limited as long as it helps to enhance the catalytic activity, and it may be, for example, a metal-based compound such as a metal halide.

As an example, the catalyst may further comprise a copper compound. The copper compound may be a compound in which an anionic species such as a halogen is bound to a copper cation. Specifically, the copper compound is one or more selected from the group consisting of tricyclohexylphosphine-copper chloride ($PCy_3CuCl$), copper chloride (CuCl), copper iodide (CuI), and copper (I)-thiophene-2-carboxylate (CuTc).

As another example, the catalyst may further comprise a sodium compound. The sodium compound may be a compound in which an anionic species such as a halogen is bound to a sodium cation. Specifically, the sodium compound may be one or more selected from the group consisting of sodium bromide (NaBr), sodium iodide (NaI), sodium acetate (NaOAc), and sodium benzoate (PhCOONa).

The catalyst may be used in an amount ranging from 1 ppm to 100 ppm, ranging from 1 ppm to 50 ppm, or ranging from 5 ppm to 20 ppm.

The catalyst is very excellent in terms of selectivity and turnover number (TON). For example, the catalyst may have a selectivity of 80% or more, 85% or more, 90% or more, or 95% or more. In addition, the catalyst may have a TON of 10,000 or more, 15,000 or more, 20,000 or more, or 25,000 or more.

In addition, the catalyst may have a conversion rate of 30% or more, 40% or more, 50% or more, 60% or more, or 70% or more.

Process for Preparing a Linear α-olefin

The present invention also provides a process for preparing a linear α-olefin, which comprises adding ethylene to an unsaturated fatty acid in the presence of the catalyst.

In the process for preparing a linear α-olefin, the unsaturated fatty acid comprises a compound represented by the following Formula 3, and the linear α-olefin may have 2 to 10 carbon atoms.

[Formula 3]

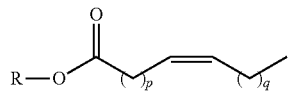

In the above formula, R is $C_{1-6}$ alkyl; and p and q are each independently an integer from 1 to 10.

In addition, in the process for preparing a linear α-olefin, the unsaturated fatty acid may be methyl oleate, and the linear α-olefin may be 1-decene.

In the preparation process, the catalyst may be used at a concentration of 1 ppm to 100 ppm.

Specifically, the catalyst may be used at a concentration of 1 ppm to 50 ppm.

More specifically, the catalyst may be used at a molar concentration of 1 ppm to 50 ppm, 1 ppm to 40 ppm, 10 ppm to 40 ppm, or 5 ppm to 20 ppm, based on the number of moles of the unsaturated fatty acid.

The preparation process may be carried out under the conditions of relatively low pressures and low temperatures.

For example, the pressure conditions of the preparation process may be in the range of 50 psi to 300 psi or 100 psi to 200 psi.

In addition, the temperature conditions of the preparation process may be in the range of 20° C. to 100° C. or 30° C. to 60° C.

In addition, in the preparation process, after ethylene is added to the unsaturated fatty acid, the reaction may be carried out for 30 minutes to 20 hours, 30 minutes to 10 hours, 30 minutes to 5 hours, or 1 hour to 3 hours.

In the preparation process, the selectivity may be 80% or more, 85% or more, 90% or more, or 95% or more.

In addition, in the preparation process, the TON may be 10,000 or more, 15,000 or more, 20,000 or more, or 25,000 or more.

In addition, in the preparation process, the conversion rate may be 30% or more, 40% or more, 50% or more, 60% or more, or 70% or more.

In addition, in the preparation process, the yield may be 20% or more, 30% or more, 40% or more, 50% or more, or 60% or more.

The methods for calculating the selectivity, TON, conversion rate, and yield are exemplified in Test Example to be described below.

MODE FOR THE INVENTION

Hereinafter, the present invention will be described in detail with reference to examples. However, the following examples are intended to illustrate the present invention. The scope of the present invention is not limited thereby.

Example 1: Preparation of Ruthenium Complex Compounds (Compounds c25 to c32)

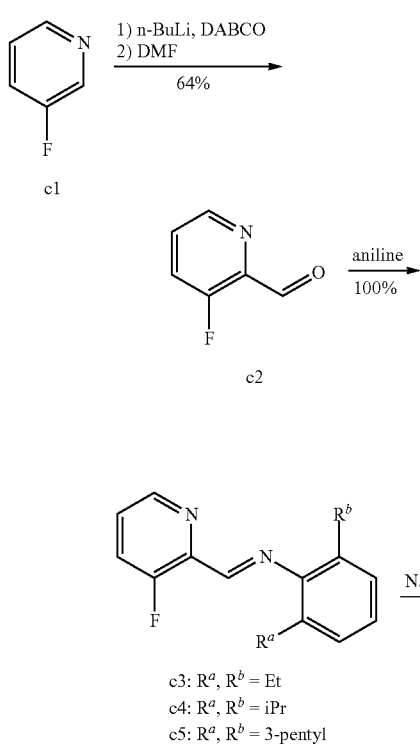

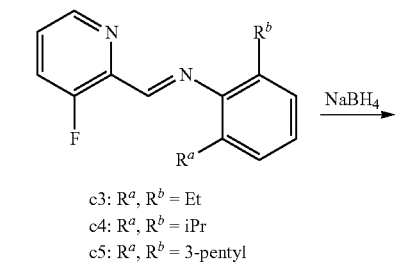

c3: $R^a$, $R^b$ = Et
c4: $R^a$, $R^b$ = iPr
c5: $R^a$, $R^b$ = 3-pentyl

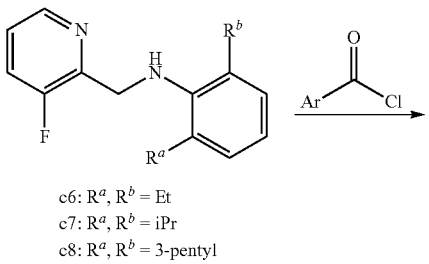

c6: $R^a$, $R^b$ = Et
c7: $R^a$, $R^b$ = iPr
c8: $R^a$, $R^b$ = 3-pentyl

-continued

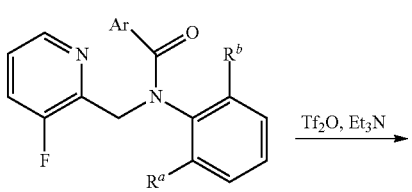

c9: $R^a, R^b$ = iPr, Ar = Ph
c10: $R^a, R^b$ = iPr, Ar = 4-tBu-Ph,
c11: $R^a, R^b$ = iPr, Ar = 4-OMe-Ph,
c12: $R^a, R^b$ = iPr, Ar = 4-F-Ph,
c13: $R^a, R^b$ = iPr, Ar = 4-$CF_3$,
c14: $R^a, R^b$ = iPr, Ar = 1-nap,
c15: $R^a, R^b$ = Et, Ar = Ph
c16: $R^a, R^b$ = 3-pentyl, Ar = Ph

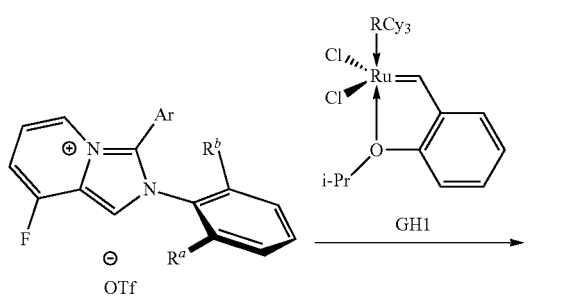

c17: $R^a, R^b$ = iPr, Ar = Ph
c18: $R^a, R^b$ = iPr, Ar = 4-tBu-Ph,
c19: $R^a, R^b$ = iPr, Ar = 4-OMe-Ph,
c20: $R^a, R^b$ = iPr, Ar = 4-F-Ph,
c21: $R^a, R^b$ = iPr, Ar = 4-$CF_3$,
c22: $R^a, R^b$ = iPr, Ar = 1-nap,
c23: $R^a, R^b$ = Et, Ar = Ph
c24: $R^a, R^b$ = 3-pentyl, Ar = Ph

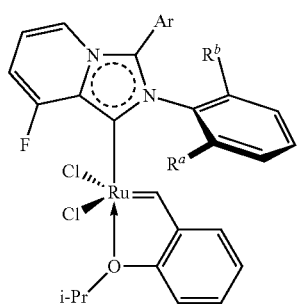

c25: $R^a, R^b$ = iPr, Ar = Ph
c26: $R^a, R^b$ = iPr, Ar = 4-tBu-Ph,
c27: $R^a, R^b$ = iPr, Ar = 4-OMe-Ph,
c28: $R^a, R^b$ = iPr, Ar = 4-F-Ph,
c29: $R^a, R^b$ = iPr, Ar = 4-$CF_3$,
c30: $R^a, R^b$ = iPr, Ar = 1-nap,
c31: $R^a, R^b$ = Et, Ar = Ph
c32: $R^a, R^b$ = 3-pentyl, Ar = Ph 3-Fluoropyridine (compound c1) was selectively lithiated and reacted with dimethylformamide (DMF) to obtain an aldehyde (compound c2). The aldehyde (compound c2) was reacted with 2,6-diethylaniline, 2,6-diisopropylaniline, and 2,6-di(3-pentyl)aniline, respectively, to form imines (compounds c3 to c5), which were reduced with $NaBH_4$ to obtain amines (compounds c6 to c8). The amines (compounds c6 to c8) were reacted with an aromatic acyl chloride to form amides (compounds c9 to c16), which were subjected to a cyclization reaction in the presence of trifluorosulfonyl anhydride ($Tf_2O$) and an amine base to obtain carbene ligands (compounds c17 to c24). The carbene ligands (compounds c17 to c24) were subjected to an exchange reaction with a phosphine ligand of a first-generation Grubbs-Hoveyda catalyst (GH1) to synthesize ruthenium catalysts (compound c25 to c32).

More specific procedures and reaction conditions for each step are described below.

Step (1) Preparation of Compound c2 n-Butyllithium (1.1 eq.) was added to a diethyl ether solution (1.1 M) of 1,4-diazabicyclo[2.2.2]octane (DABCO) (1 eq.) and stirred for 1 hour. The mixture was cooled at −60° C., and a solution (2 M, 1 eq.) of 3-fluoropyridine (compound c1) was added dropwise thereto. The mixture was stirred at −60° C. for 2 hours, and dimethylformamide (DMF, 2 M, 2 eq.) was added thereto. The mixture was stirred at −60° C. for 1 hour and purified by column chromatography to obtain compound c2.

Step (2) Preparation of Compounds c3 to c5

Compound c2 (1 eq.) and aniline (1 eq.) were dissolved in ethanol (0.5 M). The mixture was stirred and left at 80° C. for 4 hours. The product was used in the next step without purification.

Step (3) Preparation of Compounds c6 to c8

$NaBH_4$ was slowly added to a methanol solution of compounds c3 to c5 at 0° C. The reaction mixture was stirred under reflux overnight. The organic phase was extracted, collected, and dried over $MgSO_4$. The solvent was removed, and the product was purified by column chromatography to obtain compounds c6 to c8.

Step (4) Preparation of Compounds c9 to c16

Compounds c6 to c8 and acyl chloride were dissolved in 1,2-dichloroethane (DCE). The reaction mixture was stirred at reflux overnight and then cooled to room temperature. The solvent was removed, and the product was purified by column chromatography to obtain respective compounds c9 to c16.

Step (5) Preparation of Compounds c17 to c24

Each of the compounds c9 to c16 (1 eq.) was dissolved in dichloromethane (DCM). Triethylamine ($Et_3N$, 1 eq.) was added dropwise to the solution at −40° C. After 5 minutes, trifluoromethanesulfonic anhydride ($Tf_2O$, 1 eq.) was carefully added thereto. The mixture was warmed to room temperature and stirred for 4 hours. The solvent was removed, and the product was purified by column chromatography to obtain respective compounds c17 to c24 as a carbene ligand.

Step (6) Preparation of Compounds c25 to c32

A benzene solution of each of compounds c17 to c24 (2 eq.) and potassium bis(trimethylsilyl)amide (KHMDS, 2.2 eq.) was stirred at room temperature for 30 minutes. The solution was filtered and added to a benzene solution of a first-generation Grubbs-Hoveyda catalyst. The mixture was filtered through a pad of celite and eluted with benzene, and the filtrate was concentrated. Thereafter, it was purified by column chromatography to obtain respective compounds c25 to c32.

Example 2: Preparation of Ruthenium Complex Compounds (Compounds c36 to c38)

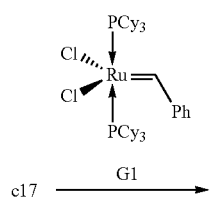

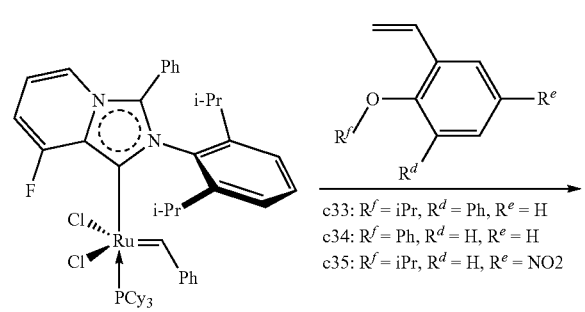

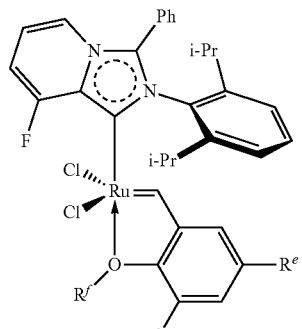

c36: $R^f$ = iPr, $R^d$ = Ph, $R^e$ = H
c37: $R^f$ = Ph, $R^d$ = H, $R^e$ = H
c38: $R^f$ = iPr, $R^d$ = H, $R^e$ = NO_2

A benzene solution of compound c17 (2 eq.) prepared in Example 1 and potassium bis(trimethylsilyl)amide (KHMDS, 2.2 eq.) was stirred at room temperature for 30 minutes. The solution was filtered and added to a benzene solution of a first-generation Grubbs catalyst. The mixture was filtered through a pad of celite and eluted with benzene, and the filtrate was concentrated. Thereafter, each of styrene compounds c33 to c35 was added thereto. The mixture was heated to 40° C. and stirred for 2 hours. Thereafter, it was purified by column chromatography to obtain respective compounds c36 to c38.

The structural formulae, yields, and $^1$H-NMR data of compounds c25 to c32 and c36 to c38 thus prepared are shown in the table below.

TABLE 1

| Comp'd | structural formula | Yield/NMR |
| --- | --- | --- |
| c25 | 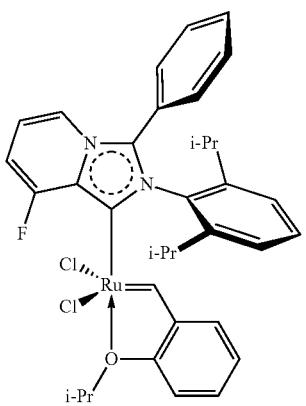 | Yield: 56%<br>$^1$H NMR (400 MHz, CD_2Cl_2) δ 16.67 (s, 1H), 7.84 (s, 1H), 7.70 (t, J = 7.8 Hz, 1H), 7.54 (t, J = 7.3 Hz, 1H), 7.38 (dd, J = 10.0, 5.6 Hz, 5H), 7.28 (d, J = 5.0 Hz, 2H), 7.01 (t, J = 8.9 Hz, 2H), 6.89 (dt, J = 11.7, 7.4 Hz, 2H), 6.47 (s, 1H), 5.19-5.09 (m, 1H), 2.47-2.31 (m, 2H), 1.81 (d, J = 6.1 Hz, 6H), 0.75 (dd, J = 8.2, 6.8 Hz, 12H). |

TABLE 1-continued

| Comp'd | structural formula | Yield/NMR |
|---|---|---|
| c26 | 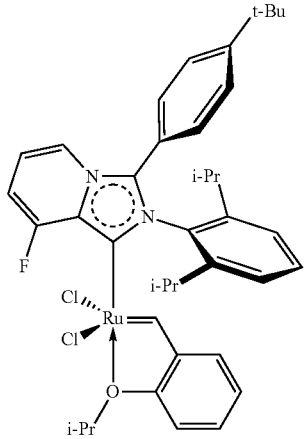 | Yield: 65%<br>¹H NMR (400 MHz, CD$_2$Cl$_2$) δ 16.63 (s, 1H), 7.71 (t, J = 7.8 Hz, 1H), 7.60-7.52 (m, 1H), 7.39 (dd, J = 8.0, 3.8 Hz, 4H), 7.17 (d, J = 5.5 Hz, 2H), 7.03 (d, J = 6.9 Hz, 1H), 6.98 (d, J = 8.3 Hz, 1H), 6.89 (dd, J = 15.8, 8.3 Hz, 2H), 5.18-5.08 (m, 1H), 2.36 (hept, J = 6.4 Hz, 2H), 1.79 (d, J = 6.1 Hz, 6H), 1.25 (s, 9H), 0.75 (d, J = 6.6 Hz, 6H), 0.70 (d, J = 6.8 Hz, 6H), |
| c27 | 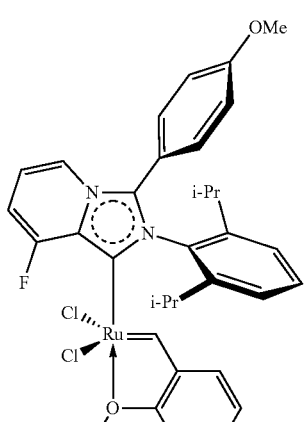 | Yield: 50%<br>¹H NMR (400 MHz, CD$_2$Cl$_2$) δ 16.68 (s, 1H), 7.78 (d, J = 7.2 Hz, 1H), 7.70 (t, J = 7.8 Hz, 1H), 7.57-7.48 (m, 1H), 7.39 (d, J = 7.8 Hz, 2H), 7.23-7.15 (m, 2H), 7.00 (dd, J = 12.2, 4.8 Hz, 2H), 6.92 (dd, J = 7.6, 7.0 Hz, 1H), 6.89-6.78 (m, 3H), 6.46 (dd, J = 9.9, 7.4 Hz, 1H), 5.13 (dt, J = 12.3, 6.1 Hz, 1H), 3.77 (s, 3H), 2.37 (dt, J = 13.4, 6.7 Hz, 2H), 1.80 (d, J = 6.1 Hz, 6H), 0.76 (d, J = 6.8 Hz, 12H). |
| c28 | 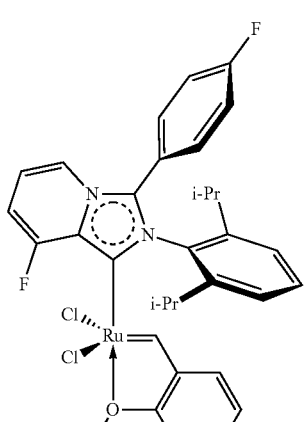 | Yield: 41%<br>¹H NMR (400 MHz, CD$_2$Cl$_2$) δ 16.65 (s, 1H), 7.80 (d, J = 7.1 Hz, 1H), 7.71 (t, J = 7.8 Hz, 1H), 7.58-7.48 (m, 1H), 7.40 (d, J = 7.9 Hz, 2H), 7.33-7.22 (m, 2H), 7.13-7.03 (m, 2H), 7.03-6.96 (m, 2H), 6.90 (ddd, J = 12.6, 11.0, 6.3 Hz, 2H), 6.52 (dd, J = 9.8, 7.5 Hz, 1H), 5.14 (dt, J = 12.3, 6.1 Hz, 1H), 2.37 (dt, J = 13.4, 6.7 Hz, 2H), 1.80 (d, J = 6.1 Hz, 6H), 0.83-0.67 (m, 12H). |

TABLE 1-continued

| Comp'd | structural formula | Yield/NMR |
|---|---|---|
| c29 | | Yield: 50%<br>¹H NMR (400 MHz, CD$_2$Cl$_2$) δ 16.62 (s, 1H), 7.92 (d, J = 7.2 Hz, 1H), 7.74 (t, J = 7.8 Hz, 1H), 7.62 (d, J = 8.4 Hz, 2H), 7.57-7.49 (m, 1H), 7.41 (dd, J = 8.0, 3.8 Hz, 3H), 7.05-6.89 (m, 3H), 6.60 (dd, J = 9.7, 7.6 Hz, 1H), 5.15 (dt, J = 12.2, 6.1 Hz, 1H), 2.38 (dt, J = 13.4, 6.7 Hz, 2H), 1.81 (d, J = 6.1 Hz, 6H), 0.76 (d, J = 6.6 Hz, 6H), 0.72 (d, J = 6.8 Hz, 6H). |
| c30 | | Yield: 44%<br>¹H NMR (400 MHz, CD$_2$Cl$_2$) δ 16.63 (s, 1H), 7.95 (dd, J = 10.7, 8.5 Hz, 2H), 7.67-7.33 (m, 7H), 7.12 (dd, J = 12.9, 5.1 Hz, 2H), 6.99 (t, J = 8.1 Hz, 3H), 6.92 (t, J = 7.4 Hz, 1H), 6.77 (td, J = 7.3, 5.3 Hz, 1H), 6.62-6.45 (m, 1H), 5.15 (dt, J = 12.2, 6.1 Hz, 1H), 2.77 (dt, J = 13.3, 6.6 Hz, 1H), 2.05 (dt, J = 20.0, 6.9 Hz, 1H), 1.83 (dd, J = 11.1, 6.1 Hz, 6H), 1.37 (d, J = 6.7 Hz, 3H), 0.86 (dd, J = 10.6, 6.8 Hz, 4H), 0.62 (d, J = 6.6 Hz, 3H), −0.21 (d, J = 6.8 Hz, 3H). |
| c31 | | Yield: 22%<br>¹H NMR (400 MHz, CD$_2$Cl$_2$) δ 16.44 (s, 1H), 7.71-7.61 (m, 1H), 7.55 (ddd, J = 8.9, 7.4, 1.7 Hz, 1H), 7.46-7.37 (m, 3H), 7.34 (d, J = 7.8 Hz, 2H), 7.31-7.24 (m, 2H), 7.05 (dd, J = 7.5, 1.5 Hz, 2H), 7.02-6.91 (m, 2H), 6.83 (td, J = 7.3, 5.3 Hz, 2H), 6.53-6.44 (m, 1H), 5.14 (dt, J = 12.1, 6.0 Hz, 1H), 2.46 (d, J = 7.4 Hz, 2H), 2.06 (dq, J = 15.2, 7.5 Hz, 2H), 1.77 (d, J = 6.1 Hz, 6H), 0.93 (t, J = 7.5 Hz, 6H). |

TABLE 1-continued

| Comp'd | structural formula | Yield/NMR |
| --- | --- | --- |
| c32 | | Yield: 56%<br>$^1$H NMR (400 MHz, CD$_2$Cl$_2$) δ 16.93 (s, 1H), 7.98 (d, J = 7.2 Hz, 1H), 7.66 (t, J = 7.8 Hz, 1H), 7.56-7.48 (m, 1H), 7.41-7.27 (m, 5H), 7.13 (dd, J = 8.1, 1.5 Hz, 2H), 7.05-6.97 (m, 2H), 6.96-6.80 (m, 2H), 6.50 (dd, J = 9.8, 7.5 Hz, 1H), 5.13 (dt, J = 12.3, 6.2 Hz, 1H), 2.53-2.40 (m, 2H), 1.81 (d, J = 6.1 Hz, 6H), 1.45-1.31 (m, 3H), 1.25-1.15 (m, 7H), 1.08 (td, J = 14.4, 7.3 Hz, 2H), 0.49 (t, J = 7.4 Hz, 6H), 0.44 (t, J = 7.4 Hz, 6H). |
| c36 | | Yield: 17%<br>$^1$H NMR (400 MHz, CD$_2$Cl$_2$) δ 16.78 (s, 1H), 7.88 (d, J = 7.2 Hz, 1H), 7.71 (t, J = 7.8 Hz, 1H), 7.60-7.53 (m, 2H), 7.45-7.31 (m, 9H), 7.31-7.26 (m, 2H), 7.03-6.93 (m, 2H), 6.86 (td, J = 7.3, 5.4 Hz, 1H), 6.50 (dd, J = 9.8, 7.5 Hz, 1H), 4.56 (hept, J = 6.3 Hz, 1H), 2.45-2.31 (m, 2H), 1.26 (d, J = 6.3 Hz, 6H), 0.80 (d, J = 6.6 Hz, 6H), 0.72 (d, J = 6.8 Hz, 6H). |
| c37 | | Yield: 7%<br>$^1$H NMR (400 MHz, CD$_2$Cl$_2$) δ 16.74 (s, 1H), 7.84 (d, J = 7.2 Hz, 1H), 7.73 (t, J = 7.8 Hz, 1H), 7.54 (d, J = 8.2 Hz, 1H), 7.51-7.32 (m, 5H), 7.28 (dd, J = 7.7, 1.9 Hz, 1H), 7.16-7.07 (m, 1H), 7.01 (t, J = 7.4 Hz, 1H), 6.83 (dd, J = 12.7, 7.3 Hz, 1H), 6.71 (d, J = 8.3 Hz, 1H), 6.40 (dd, J = 9.7, 7.5 Hz, 1H), 2.39 (dt, J = 13.5, 6.8 Hz, 2H), 0.81 (d, J = 6.6 Hz, 6H), 0.76 (d, J = 6.8 Hz, 6H). |

TABLE 1-continued

| Comp'd | structural formula | Yield/NMR |
|---|---|---|
| c38 | | Yield: 4%<br>$^1$H NMR (400 MHz, CD$_2$Cl$_2$) δ 16.57 (s, 1H), 8.43 (dd, J = 9.1, 2.7 Hz, 1H), 7.88 (d, J = 7.1 Hz, 1H), 7.85-7.74 (m, 2H), 7.49-7.33 (m, 4H), 7.28 (dd, J = 8.0, 1.7 Hz, 2H), 7.10 (d, J = 9.1 Hz, 1H), 6.89 (td, J = 7.3, 5.4 Hz, 1H), 6.54 (dd, J = 9.9, 7.5 Hz, 1H), 5.24 (dd, J = 12.1, 6.1 Hz, 1H), 2.34 (dt, J = 13.5, 6.7 Hz, 2H), 1.85 (d, J = 6.1 Hz, 6H), 0.74 (dd, J = 6.7, 1.7 Hz, 12H). |

Comparative Example 1

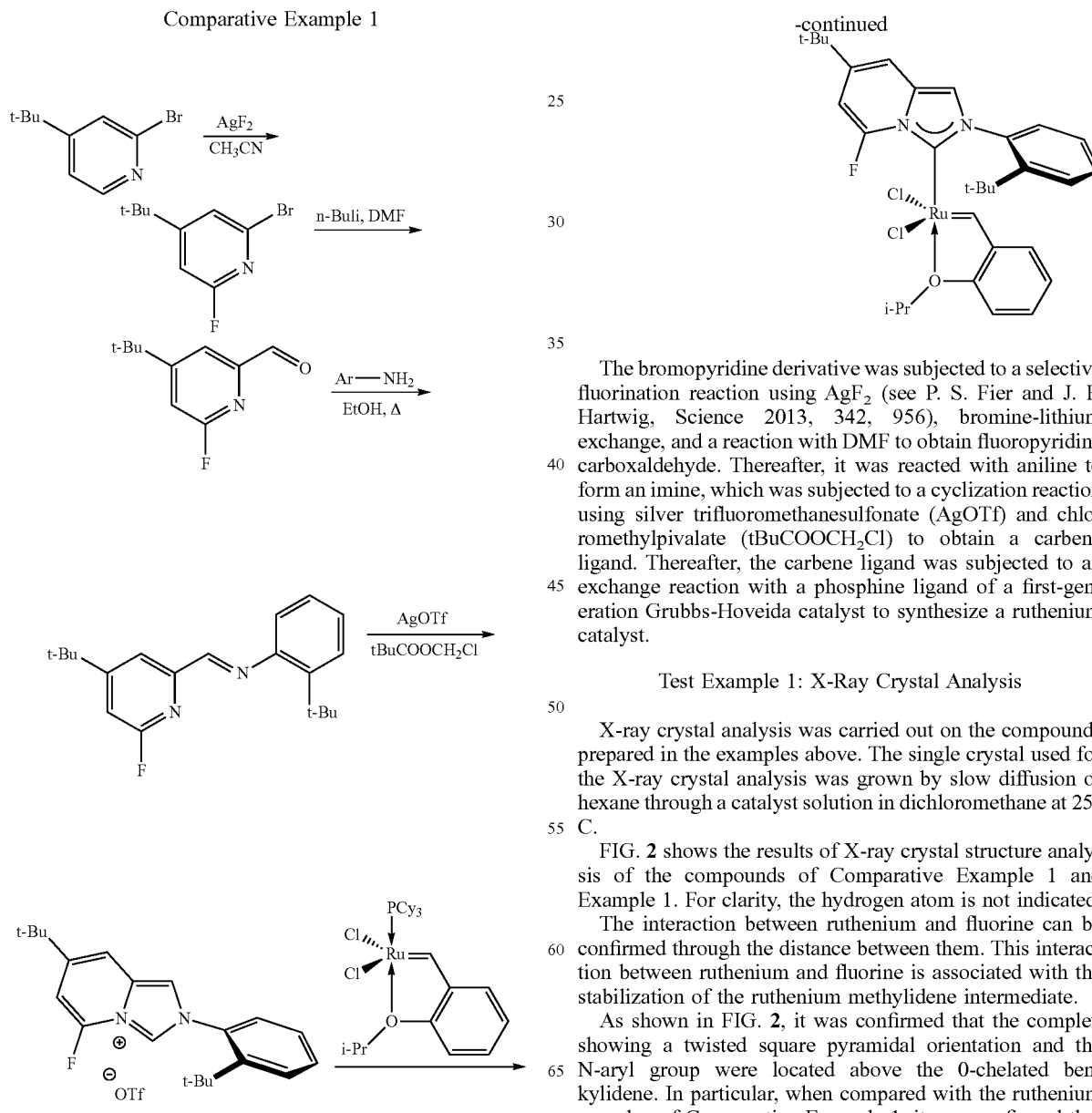

The bromopyridine derivative was subjected to a selective fluorination reaction using AgF$_2$ (see P. S. Fier and J. F. Hartwig, Science 2013, 342, 956), bromine-lithium exchange, and a reaction with DMF to obtain fluoropyridine carboxaldehyde. Thereafter, it was reacted with aniline to form an imine, which was subjected to a cyclization reaction using silver trifluoromethanesulfonate (AgOTf) and chloromethylpivalate (tBuCOOCH$_2$Cl) to obtain a carbene ligand. Thereafter, the carbene ligand was subjected to an exchange reaction with a phosphine ligand of a first-generation Grubbs-Hoveida catalyst to synthesize a ruthenium catalyst.

Test Example 1: X-Ray Crystal Analysis

X-ray crystal analysis was carried out on the compounds prepared in the examples above. The single crystal used for the X-ray crystal analysis was grown by slow diffusion of hexane through a catalyst solution in dichloromethane at 25° C.

FIG. 2 shows the results of X-ray crystal structure analysis of the compounds of Comparative Example 1 and Example 1. For clarity, the hydrogen atom is not indicated.

The interaction between ruthenium and fluorine can be confirmed through the distance between them. This interaction between ruthenium and fluorine is associated with the stabilization of the ruthenium methylidene intermediate.

As shown in FIG. 2, it was confirmed that the complex showing a twisted square pyramidal orientation and the N-aryl group were located above the 0-chelated benkylidene. In particular, when compared with the ruthenium complex of Comparative Example 1, it was confirmed that the Ru—F1 distance and the Ru—O1 distance were further increased in the ruthenium complex of Example 1, and the N1-C1-Ru angle was increased. It is understood that, in the compound of Example 1, $R^1$ is fluoro, and $R^5$ and $R^6$ are benzene rings in Formula 1, whereby steric interaction was maximized, as compared with the case where $R^5$ is hydrogen in the ruthenium complex compound of Comparative Example 1.

Test Example 2: NMR Analysis

In order to analyze the electronic properties of the carbene ligands prepared in Example 1 and Comparative Example 1, a Se complex was synthesized, and $^{77}$SE-NMR was carried out. The results are shown in FIG. 3.

Figure 3:
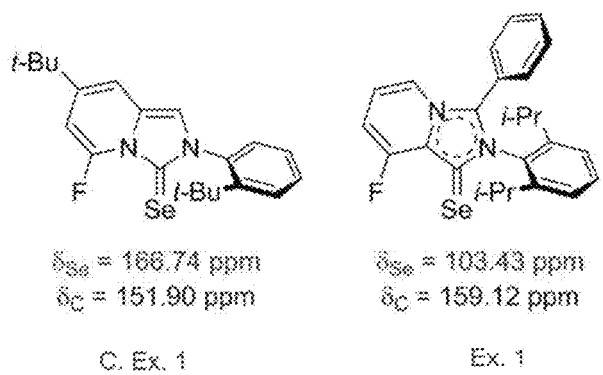
FIG. 3 shows the results of a $^{77}$Se-NMR analysis of the NHC ligand prepared in Comparative Example 1 and Example 1.

As shown in FIG. 3, the $^{77}$Se-NMR signals of the selenium complex of the respective carbene ligands prepared in Comparative Example 1 and Example 1 were measured to be 166.74 ppm and 103.43 ppm, respectively. That is, the selenium complex of the carbene ligand prepared in Example 1 exhibited a signal at a high up-field chemical shift as compared with the carbene ligand prepared in Comparative Example 1. Thus, it is expected to be a strong electron donating ligand as a weak π-acceptor.

Test Example 3: Evaluation of the Catalyst Performance in an Ethenolysis Reaction of Methyl Oleate An ethenolysis reaction of methyl oleate was carried out using each of the compounds in the example as catalysts.

Specifically, as shown in the reaction scheme below, methyl oleate (compound 11, 1 mmole) was reacted with 150 psi of $C_2H_4$ (purity 99.95%) in the presence of a catalyst (0.005% by mole, 50 ppm) at 40° C. for 1 hour to carry out an ethenolysis reaction to obtain linear α-olefins (compounds 12 and 13) and other products (compounds 14 and 15).

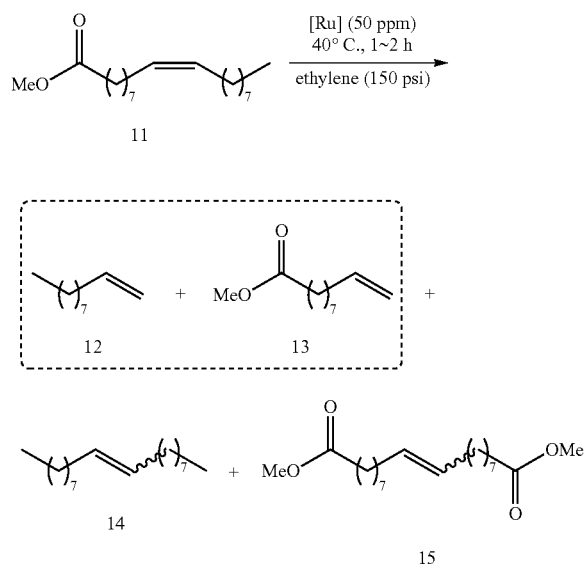

In the above reaction, the catalyst performance was evaluated as follows. The results are summarized in the table below.

Conversion (%)=[1−(final number of moles of compound 11/initial number of moles of compound 11)]×100

Selectivity (%)=(total number of moles of compounds 12 and 13)/[(total number of moles of compounds 12 and 13)+(total number of moles of compounds 14 and 15)×2]

(The conversion and selectivity were determined by GC using tridecane as an internal standard.)

Yield (%)=conversion×selectivity/100

TON (turnover number)=yield×(initial moles of compound 11/moles of the catalyst)/100

TABLE 2

| Number | Catalyst | Conversion (%) | Selectivity (%) | Yield (%) | TON |
|---|---|---|---|---|---|
| 1 | Compound c25 | 72 | 94 | 67 | 13400 |
| 2 | Compound c26 | 64 | 95 | 61 | 12200 |
| 3 | Compound c27 | 73 | 94 | 68 | 13600 |
| 4 | Compound c28 | 71 | 95 | 68 | 13600 |
| 5 | Compound c29 | 72 | 94 | 68 | 13600 |
| 6 | Compound c30 | 71 | 95 | 67 | 13500 |
| 7 | Compound c31 | 23 | 86 | 20 | 4000 |

As can be seen from the above table, when compound c25 having an asymmetric NHC ligand was used as a catalyst, it showed high selectivity in the process of α-olefin synthesis as compared with the known selectivity (30-40%) for the conventional Grubbs-Hoveyda type Ru catalyst having a symmetric NHC ligand. In addition, when compounds c26 to c30 having an asymmetric structure of an NHC ligand were used as a catalyst (Nos. 2 to 6), it showed high selectivity in the process of α-olefin synthesis similarly to compound c25. In addition, in order to investigate the steric effect of the aImPy ligand, compound c31 (No. 7) was tested under the same reaction conditions. As a result, it showed low conversion, low selectivity, and low turnover number as compared with compound c25. It is understood that, as the steric hindrance of the aryl group is reduced, the stability of the catalyst is lowered and the self-metathesis reaction is higher.

Test Example 4: Evaluation of the Catalyst Performance According to Reaction Conditions The ethenolosis reaction of methyl oleate was carried out in the same manner as in Test Example 3 using compound c25 prepared in Example 1 as a catalyst, except that the amount of catalyst added and temperature, and time during the reaction were adjusted as shown in the table below. The catalyst performance during the reaction was evaluated in the same manner and standard as in Test Example 3. The results are summarized in the table below.

TABLE 3

| Number | Amount of catalyst (ppm) | Pressure (psi) | Temp. (° C.) | Time (hr) | Conversion (%) | Selectivity (%) | Yield (%) | TON |
|---|---|---|---|---|---|---|---|---|
| 1 | 50 | 150 | 40 | 1 | 71 | 94 | 67 | 13,400 |
| 2 | 30 | 150 | 40 | 3 | 63 | 95 | 60 | 20,000 |
| 3 | 20 | 150 | 40 | 12 | 34 | 97 | 33 | 16,500 |
| 4 | 10 | 150 | 40 | 20 | 4 | 98 | 4 | 4,000 |
| 5 | 50 | 150 | 60 | 1 | 69 | 94 | 65 | 13,000 |
| 6 | 50 | 150 | 80 | 1 | 60 | 93 | 56 | 11,200 |

As can be seen from the above table, when the amount of catalyst was 30 ppm, it showed a high TON of up to 20,000 at 40° C. (No. 2). When the amount of catalyst was less than this (Nos. 3 and 4), the effect of the catalyst was gradually decreased. In addition, even if the reaction temperature was raised to 60° C. and 80° C., the catalyst activity was not significantly reduced. Thus, the catalyst had high thermal stability in an ethylene atmosphere (Nos. 5 and 6).

Test Example 5: Evaluation of the Catalyst Performance According to Additives

The ethenolosis reaction of methyl oleate was carried out in the same manner as in Test Example 3 using compound c25 prepared in Example 1 as a catalyst, except that various additives were used and the amount of catalyst added and temperature and time during the reaction were adjusted as shown in the table below. The catalyst performance during the reaction was evaluated in the same manner and standard as in Test Example 3. The results are summarized in the table below.

TABLE 4

| Number | Amount of catalyst (ppm) | Additive | Temp. (° C.) | Time (hr) | Conversion (%) | Selectivity (%) | Yield (%) | TON |
|---|---|---|---|---|---|---|---|---|
| 1 | 10 | Not added | 40 | 20 | 4 | 98 | 4 | 4,000 |
| 2 | 10 | PCy$_3$CuCl 10 ppm | 40 | 3 | 46 | 96 | 44 | 44,000 |
| 3 | 5 | PCy$_3$CuCl 5 ppm | 40 | 3 | 30 | 97 | 29 | 58,000 |
| 4 | 3 | PCy$_3$CuCl 6 ppm | 40 | 9 | 19 | 97 | 19 | 63,000 |
| 5 | 2 | PCy$_3$CuCl 4 ppm | 40 | 18 | 12 | 98 | 11 | 57,000 |
| 6 | 1 | PCy$_3$CuCl 2 ppm | 40 | 24 | 5 | 97 | 5 | 51,000 |
| 7 | 5 | CuCl 5 ppm | 40 | 3 | 13 | 97 | 12 | 24,000 |
| 8 | 5 | CuI 5 ppm | 40 | 3 | 16 | 96 | 15 | 30,000 |
| 9 | 10 | CuI 10 ppm | 40 | 3 | 28 | 97 | 27 | 27,000 |
| 10 | 5 | CuTc 5 ppm | 40 | 3 | 17 | 93 | 16 | 32,500 |

As can be seen from the above table, when used in combination with additives, it showed excellent performance even in a smaller amount of catalyst (Nos. 2 and 3). In particular, when combined with PCy$_3$CuCl, a high TON of up to 63,000 was achieved at 40° C. with a catalytic amount of 3 ppm (No. 4). In addition, even if the amount of catalyst was reduced to 1 ppm, the catalyst was active, and the stability of the catalyst could be confirmed (Nos. 5 and 6).

Test Example 6: Evaluation of the Catalyst Performance According to Change of Ligand The ethenolosis reaction of methyl oleate was carried out in the same manner as in Test Example 3, except that the catalyst type, amount of catalyst added, and pressure, temperature, and time during the reaction were adjusted as shown in the table below. The catalyst performance during the reaction was evaluated in the same manner and conditions as in Test Example 3. The results are summarized in the table below.

TABLE 5

| Number | Catalyst compound | Amount of catalyst (ppm) | Pressure (psi) | Temp. (° C.) | Time (hr) | Conversion (%) | Selectivity (%) | Yield (%) | TON |
|---|---|---|---|---|---|---|---|---|---|
| 1 | c36 | 50 | 150 | 40 | 1 | 60 | 96 | 57 | 11,400 |
| 2 | c36 | 30 | 150 | 40 | 1 | 50 | 95 | 48 | 16,000 |
| 3 | c36 | 20 | 150 | 40 | 1 | 40 | 95 | 38 | 19,000 |
| 4 | c36 | 20 | 80 | 25 | 3 | 50 | 90 | 45 | 22,500 |
| 5 | c36 | 15 | 150 | 40 | 1 | 31 | 97 | 30 | 20,000 |
| 6 | c36 | 15 | 150 | 40 | 3 | 41 | 95 | 42 | 28,000 |
| 7 | c36 | 10 | 150 | 40 | 3 | 14 | 98 | 14 | 14,000 |
| 8 | c36 | 10 | 150 | 40 | 8 | 29 | 96 | 28 | 28,000 |
| 9 | c37 | 10 | 150 | 40 | 6 | 15 | 97 | 15 | 15,000 |

As can be seen from the above table, when the amount of catalyst was 10 ppm, it showed a high TON of up to 28,000 at 40° C. When the amount of catalyst was less than this, the catalyst activity was not significantly decreased (Nos. 1 to 8).

Test Example 7: Evaluation of the Catalyst Performance According to Change in Catalyst and Additives The ethenolosis reaction of methyl oleate was carried out in the same manner as in Test Example 3, except that the catalyst type, amount of catalyst added, and pressure, temperature, and time during the reaction were adjusted as shown in the table below. The catalyst performance during the reaction was evaluated in the same manner and conditions as in Test Example 3. The results are summarized in the table below.

TABLE 6

| Number | Catalyst | Additive | Conversion (%) | Selectivity (%) | Yield (%) | TON |
|---|---|---|---|---|---|---|
| 1 | c25 5 ppm | PCy₃CuCl 5 ppm | 30 | 97 | 29 | 58000 |
| 2 | c26 5 ppm | PCy₃CuCl 5 ppm | 14 | 98 | 14 | 28000 |
| 3 | c27 5 ppm | PCy₃CuCl 5 ppm | 14 | 98 | 14 | 28000 |
| 4 | c28 5 ppm | PCy₃CuCl 5 ppm | 27 | 97 | 26 | 52000 |
| 5 | c29 5 ppm | PCy₃CuCl 5 ppm | 25 | 97 | 24 | 48000 |
| 6 | c30 5 ppm | PCy₃CuCl 5 ppm | 19 | 98 | 19 | 37000 |
| 7 | c32 5 ppm | PCy₃CuCl 5 ppm | 20 | 99 | 20 | 40000 |
| 8 | c36 5 ppm | PCy₃CuCl 5 ppm | 19 | 97 | 19 | 37000 |
| 9 | c38 5 ppm | PCy₃CuCl 5 ppm | 26 | 99 | 26 | 51000 |

As can be seen from the above table, when used in combination with PCy₃CuCl as an additive, it showed excellent performance even when the amount of catalyst was reduced to 5 ppm in most catalysts. It showed a selectivity of 97% or more (up to 99% or more) and a high TON of 28,000 or more (up to 58,000) at 40° C. (Nos. 1 to 9).

Comparison of the Performance with the Conventional Ruthenium Complex Compounds

The following compounds 21 to 23 can be synthesized by the method of Richard L. Pederson, et al. [Clean 2008, 36 (8), 669-673], and the following compound 24 can be synthesized by the method of Robert H. Grubbs, et al. [J. Am. Chem. Soc. 2011, 133, 7490-7496].

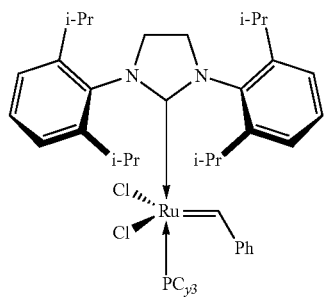

21

-continued

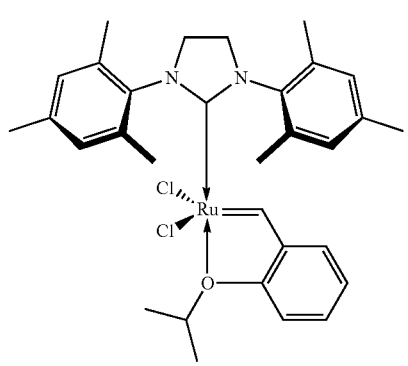

22

-continued

23

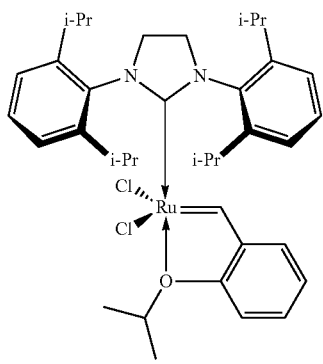

24

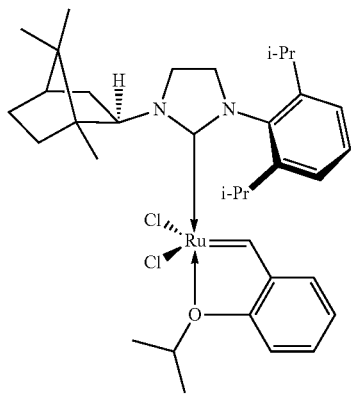

Based on the test results described in these documents, the catalytic performance of compounds 21 to 24 in the ethenolysis reaction of methyl oleate is summarized in the table below.

TABLE 7

| Catalyst | Amount of catalyst (ppm) | Conversion (%) | Selectivity (%) | Yield (%) | TON |
|---|---|---|---|---|---|
| Compound 21 | 10 | 61 | 36 | 22 | 22,000 |
| Compound 22 | 100 | 60 | 33 | 20 | 2,000 |
| Compound 23 | 100 | 70 | 56 | 39 | 3,900 |
| Compound 23 | 35 | 69 | 57 | 39 | 11,000 |
| Compound 24 | 100 | 15 | 95 | 15 | 1,460 |
| Compound 24 | 500 | 48 | 95 | 15 | 913 |

As can be seen from the above table, compounds 21 to 23 having a symmetrical NHC ligand were inferior to the ruthenium complex compounds of Formula 1 of the present invention in terms of selectivity and yield. For compound 24, the reaction yield and TON were very poor.

The invention claimed is:

1. A ruthenium complex compound represented by the following Formula 1:

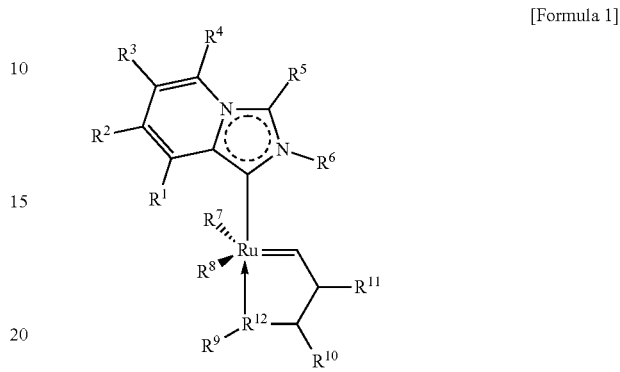

[Formula 1]

in the above formula, $R^1$ is halogen, amino, $C_{1-3}$ alkyl, or $C_{1-3}$ alkoxy;

$R^2$, $R^3$, and $R^4$ are each independently hydrogen, halogen, amino, $C_{1-5}$ alkyl, or $C_{1-5}$ alkoxy;

$R^5$ and $R^6$ are each independently a $C_{5-10}$ carbocycle or a 5-10-membered heterocycle;

$R^7$ and $R^8$ are each independently halogen;

$R^9$ is $C_{1-10}$ alkyl, a $C_{5-10}$ carbocycle, or a 5-10-membered heterocycle;

$R^{10}$ and $R^{11}$ are each independently $C_{1-10}$ alkyl or fused to each other to form a $C_{5-10}$ carbocycle, or a 5-10-membered heterocycle; and $R^{12}$ is N or O;

wherein the alkyl and the alkoxy are each independently unsubstituted or substituted with at least one of halogen, hydroxy, and amino;

the carbocycle and the heterocycle are each independently a saturated or unsaturated ring, which is unsubstituted or substituted with at least one selected from the group consisting of halogen, nitro, $C_{1-5}$ alkyl, halo $C_{1-5}$ alkyl, $C_{1-5}$ alkoxy, and phenyl; and the heterocycle contains at least one heteroatom selected from N, S, and O.

2. The ruthenium complex compound of claim 1, wherein $R^1$ is halogen.

3. The ruthenium complex compound of claim 1, wherein $R^2$ and $R^4$ are hydrogen.

4. The ruthenium complex compound of claim 1, wherein $R^5$ and $R^6$ are each independently a $C_{6-10}$ carbocycle or a 5-10-membered heterocycle having aromaticity; and the carbocycle and the heterocycle are each independently unsubstituted or substituted with at least one selected from the group consisting of halogen, nitro, $C_{1-5}$ alkyl, halo $C_{1-5}$ alkyl, and $C_{1-5}$ alkoxy.

5. The ruthenium complex compound of claim 1, which comprises a mesoionic structure.

6. A ruthenium complex compound represented by Formula 1a:

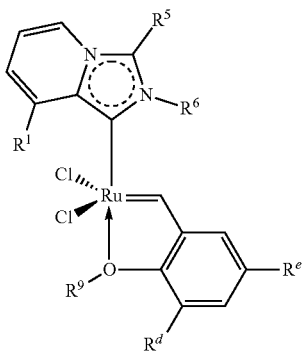

[Formula 1a]

in the above formula,
$R^1$ is halogen, amino, $C_{1-3}$ alkyl, halo $C_{1-3}$ alkyl, or $C_{1-3}$ alkoxy;
$R^5$ and $R^6$ are each independently a $C_{6-10}$ carbocycle or a 5-10-membered heterocycle having aromaticity;
$R^9$ is $C_{1-3}$ alkyl or phenyl; and
$R^d$ and $R^e$ are each independently hydrogen, nitro, or phenyl;
wherein the carbocycle and the heterocycle are each independently unsubstituted or substituted with at least one selected from the group consisting of halogen, nitro, $C_{1-5}$ alkyl, halo $C_{1-5}$ alkyl, and $C_{1-5}$ alkoxy; and the heterocycle contains at least one heteroatom selected from N, S, and O.

7. A ruthenium complex compound represented by Formula 1b:

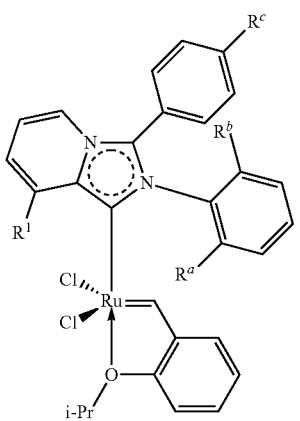

[Formula 1b]

in the above formula, $R^1$ is halogen; and $R^a$, $R^b$, and $R^c$ are each independently hydrogen, halogen, $C_{1-5}$ alkyl, halo $C_{1-5}$ alkyl, or $C_{1-5}$ alkoxy.

8. The ruthenium complex compound of claim 7, which, in X-ray crystal structure analysis, exhibits a distance of 2.85 to 3.15 Å between ruthenium (Ru) and substituent $R^1$.

9. A ligand for the preparation of a ruthenium complex compound, which comprises a compound represented by the following Formula 2:

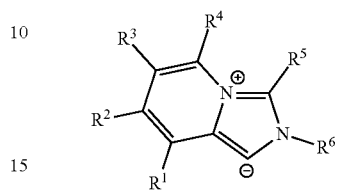

[Formula 2]

in the above formula, $R^1$ to $R^6$ are as defined in claim 1.

10. A catalyst comprising the ruthenium complex compound of claim 1.

11. The catalyst of claim 10, which is used in an alkenolysis reaction.

12. The catalyst of claim 10, which is used in a metathesis reaction by ethenolysis of a linear or cyclic alkene compound.

13. The catalyst of claim 10, which is used in an intramolecular cross-metathesis reaction, a ring-opening metathesis reaction, a ring-closing metathesis reaction, a ring-opening metathesis polymerization reaction, or acrylic diene-metathesis polymerization reaction.

14. The catalyst of claim 10, which is used in a depolymerization reaction or an ethenolysis reaction of an unsaturated linear polymer containing a double bond.

15. The catalyst of claim 10, which further comprises a copper compound.

16. A process for preparing a linear α-olefin, which comprises adding ethylene to an unsaturated fatty acid in the presence of the catalyst of claim 10.

17. The process for preparing the linear α-olefin of claim 16, wherein the unsaturated fatty acid comprises a compound represented by the following Formula 3, and the linear α-olefin has 2 to 10 carbon atoms:

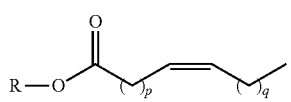

[Formula 3]

in the above formula, R is $C_{1-6}$ alkyl; and p and q are each independently an integer from 1 to 10.

18. The process for preparing the linear α-olefin of claim 16, comprises using the catalyst at a molar concentration of 1 ppm to 50 ppm based on the number of moles of the unsaturated fatty acid.

* * * * *